United States Patent [19]

Beriger Ernst

[11] Patent Number: 4,694,014
[45] Date of Patent: Sep. 15, 1987

[54] NEMATICIDAL COMPOSITIONS

[75] Inventor: Beriger Ernst, Allschwil, Switzerland

[73] Assignee: Ciba-Geigy Corporation, Ardsley, N.Y.

[21] Appl. No.: 912,904

[22] Filed: Sep. 26, 1986

[30] Foreign Application Priority Data

Sep. 30, 1985 [CH] Switzerland .................... 4214/85

[51] Int. Cl.$^4$ ............... C07D 271/10; C07D 285/10; A01N 43/82
[52] U.S. Cl. ............................... 514/363; 514/364; 548/136; 548/144
[58] Field of Search ............... 548/136, 144; 514/361, 514/363, 364

[56] References Cited

U.S. PATENT DOCUMENTS 4,269,984 5/1981 Felix ........................... 548/142

OTHER PUBLICATIONS

J. Am. Chem. Soc., 78, 4975 (1956).
J. Prakt. Chem., 93, 49 (1916).
J. Org. Chem., 23, 1021 (1958).
J. Heterocyclic Chem., 19, 541 (1982).

Primary Examiner—Robert Gerstl
Attorney, Agent, or Firm—Meredith C. Findlay

[57] ABSTRACT

The invention relates to novel compounds of the formulae

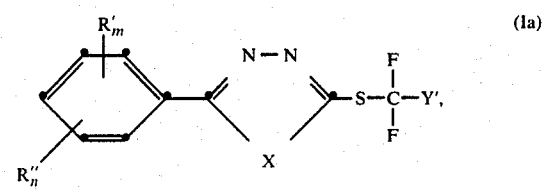

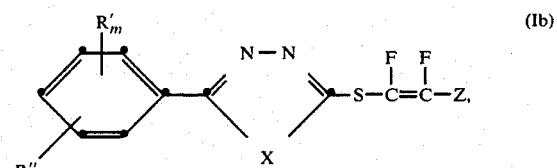

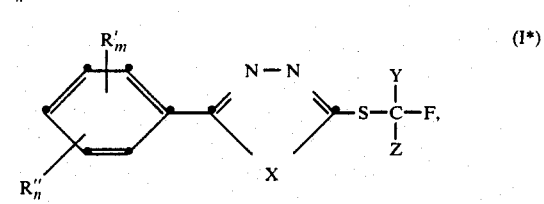

in which formulae
R' is $C_1$–$C_5$alkyl, $C_1$–$C_5$alkoxy, halogen or trifluoromethyl,
R" is $C_1$–$C_5$alkyl or halogen,
m is 1 ot 3 and n is 0 to 1,
X is oxygen or sulfur,
Y is hydrogen, fluorine, trifluoromethyl or the group HC(F)Z,
Y' is hydrogen or the group $CHF_2$ and
Z is fluorine or trifluoromethyl,
as active ingredients for controlling nematodes which parasitise on plants and for protecting cultivated plants from damage caused by nematode attack.

16 Claims, No Drawings

NEMATICIDAL COMPOSITIONS

The present invention relates to novel substituted alkylmercaptophenyl-1,3,4-oxadiazole and alkylmercaptophenyl-1,3,4-thiadiazole derivatives, to the preparation thereof and to nematicidal compositions which contain, as active ingredient, at least one of these compounds. The invention further relates to the use of the novel compounds and compositions for controlling nematodes, in particular plant-destructive nematodes.

The present invention relates to compounds of the following general formulae

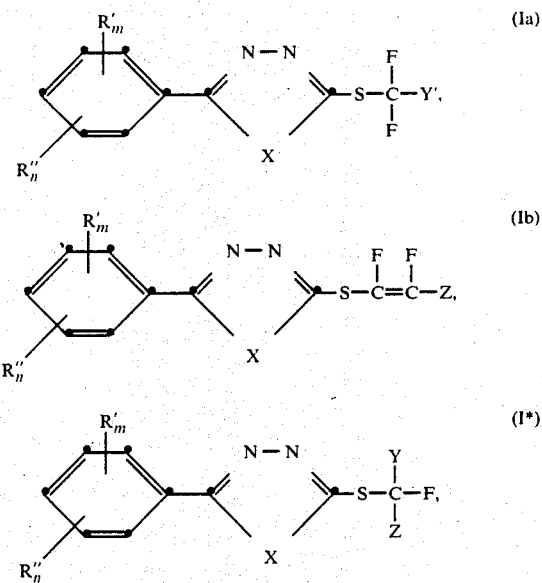

in which formulae

R' is $C_1$–$C_5$alkyl, $C_1$–$C_5$alkoxy, halogen or trifluoromethyl,

R" is $C_1$–$C_5$alkyl or halogen, m is 1 to 3 and n is 0 or 1,

X is oxygen or sulfur,

Y is hydrogen, fluorine, trifluoromethyl or the group HC(F)Z,

Y' is hydrogen or the group $CHF_2$ and

Z is fluorine or trifluoromethyl, and to the acid addition salts thereof with organic or inorganic acids.

Alkyl by itself or as moiety of another group such as alkoxy will be understood as meaning straight chain and branched alkyl groups. Such groups include methyl, ethyl and the isomers or propyl, butyl and pentyl, in particular methyl, ethyl, n-propyl, isopropyl, isobutyl or n-pentyl. Halogen is fluorine, chlorine, bromine or iodine, with fluorine or chlorine being preferred.

Examples of salt-forming inorganic acids are hydrohalic acids such as hydrofluoric acid, hydrochloric acid, hydrobromic acid or hydriodic acid, as well as sulfuric acid, phosphoric acid, phosphorous acid an nitric acid; examples of salt-forming organic acids are acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid and 2-acetoxybenzoic acid.

Oxadiazole and thiadiazole derivatives described as nematicidally effective are known. U.S. Pat. No. 3,770,754 discloses such compounds with hetero atoms in 1,2,4-position, whereas U.S. Pat. No. 4,454,147 describes 1,3,4-thiadiazole derivatives in which, in comparison with the compounds of this invention, the heterocycle is substituted by a chlorine atom instead of by mercapto groups. As nematicides these known compounds have so far not been able to meet to the full extent the demands made of them in practice.

With the compounds of formulae Ia, Ib and I* of the present invention it is now possible to make a valuable contribution to controlling plant namatodes which cause considerable agricultural damage to plants. By controlling such nematodes, losses of crops of cultivated plants such as potatoes, cereals, carrots, rape, cabbage and vegetables and also damage caused in nurseries and to ornamentals can be inhibited on a long-term basis. The compounds of the present invention are distinguished in particular by the fact that they effectively control soil nematodes which parasitise in roots, e.g. those nematodes of the genera Heterodera and Globodera (cystogenic nematodes), Meloidogyne (root-knot nematodes) and also of the genera Pratylenchus, Paratylenchus, Longidorus, Trichodorus and Xiphinema. The nematode genera Ditylenchus (stem parasites), Aphelenchoides (bud and leaf nematodes) and Anguina (seed-gall nametodes) can also be effectively controlled with the compounds of this invention.

With the compounds of formulae Ia, Ib and I* preferably particularly harmful nematode species of the genus Meloidogyne, e.g. *Meloidogyne incognita*, of the genus Heterodera, e.g. *Heterodera glycines* (soybean cyst nematode), of the genus Globodera, e.g. *Globodera rostochienis* (potato cyst nematode) and also of the genus Radopholus, an endoparasitic root nematode which damages banana plants, can be sucessfully controlled.

In order to control plant nematodes and to keep the plants healthy, the novel compounds may be used curatively, preventively or systemically. They have a wide activity spectrum against the various nematode species and therefore meet the requirements made of them in practice. The nematicidal mode of action of the compounds of the present invention is coupled, advantageously, with their low phytotoxicity, thereby particularly satisfying the general desire for a reduction in damage to the environment.

Within the scope of the present invention, the following compounds of formulae Ia, Ib and I* are preferred:

(1) compounds wherein R' is $C_1$–$C_2$alkyl, $C_1$–$C_2$alkoxy, halogen or trifluoromethyl and R" is $C_1$–$C_4$alkyl or halogen and m is 1 or 2;

(2) compounds wherein R' is methyl, methoxy, fluorine or chlorine and R" is fluorine or chlorine, Y is hydrogen and Z is fluorine.

Preferred individual compounds 2-difluoromethylthio-5-(4'-methoxyphenyl)-1,3,4-oxadiazole;

2-difluoromethylthio-5-(4'-methoxyphenyl)-1,3,4-thiadiazole;

2-difluoromethylthio-5-(2'-fluorophenyl)-1,3,4-thiadiazole;

2-difluoromethylthio-5-(4'-chlorophenyl)-1,3,4-thiadiazole;

2-difluoromethylthio-5-(2'-methylphenyl)-1,3,4-
thiadiazole;
2-difluoromethylthio-5-(2',4'-dichlorophenyl)-1,3,4-
thiadiazole;
2-difluoromethylthio-5-(2'6'-difluorophenyl)-1,3,4-
thiadiazole;
2-difluoromethylthio-5-(4'-fluorophenyl)-1,3,4-
thiadiazole;
2-difluoromethylthio-5-(3'-chlorophenyl)-1,3,4-
thiadiazole.

In accordance with the present invention, the compounds of formulae Ia, Ib and I* are prepared by (a) reacting, in a condensation reaction, a compound of formula IIa

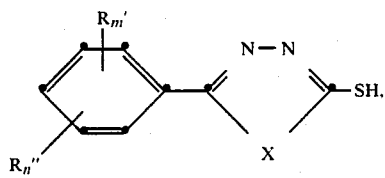
(IIa)

or a compound of formula IIb

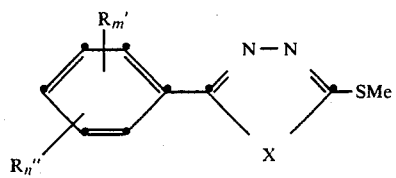
(IIb)

with a compound of formula IIIa

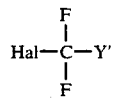
(IIIa)

or with a compound of formula III*

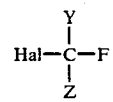
(III*)

in an inert solvent or solvent mixture, at elevated temperature, in the absence or presence of a catalyst and, if desired, under increased pressure, the reaction of a compound of formula IIa being carried out in the presence of a base, or (b) reacting, in an addition reaction, a compound of formula IIa

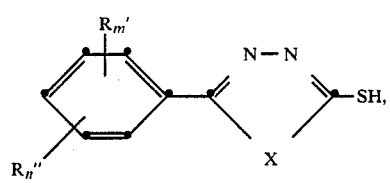
(IIa)

with a compound of formula IIIb

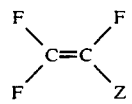
(IIIb)

in an inert solvent or solvent mixture, at elevated temperature, in the absence or presence of a catalyst and, if desired, under increased pressure, said reaction affording a compound of formula Ia*

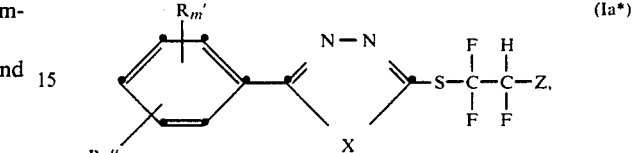
(Ia*)

or a compound of formula Ib

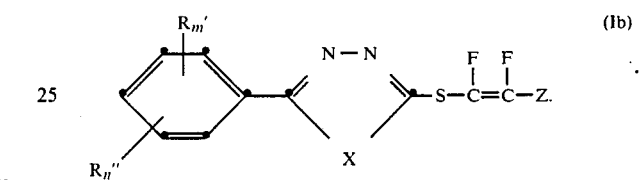
(Ib)

In the above formulae IIa, IIb, Ia*, Ib, III*, IIIa and IIIb, Me is an alkali metal or ammonium, Hal is halogen, preferably chlorine, bromine or iodine, and R', R", m, n, Y, Y' and Z are as defined for formulae Ia, Ib and I*.

Examples of solvents or diluents suitable for the preparation of the compounds of this invention are ethers and ethereal compounds such as dialkyl ethers (diethyl ether, diisopropyl ether, tert-butylmethyl ether etc.), anisole, dioxane, tetrahydrofuran; aliphatic and aromatic hydrocarbons such as benzene, toluene, petroleum ether; halogenated hydrocarbons such as chlorobenzene, mehylene chloride, chloroform, ethylene chloride, carbon tetrachloirde, tetrachloroethylene; nitriles such as acetonitrile, propionitrile; N,N-dialkylated amides such as dimethylformamide; dimethyl sulfoxide; ketones such as acetone, diethyl ketone, methyl ethyl ketone; and also water and alcohols such as methanol, ethanol, isopropanol or butanol; and, generally, mixtures of such solvents with one another.

Suitable bases are both organic and inorganic bases; e.g. preferably tertiary amines such as trialkylamines (trimethylamine, triethylamine, tripropylamine etc.), as well as oxides, hydroxides, carbonates and bicarbonates of alkali metals and alkaline earth metals (e.g. CaO, BaO, NaOH, KOH, Ca(OH)$_2$, KHCO$_3$, NaHCO$_3$, Ca(HCO$_3$)$_2$, K$_2$CO$_3$, Na$_2$CO$_3$ etc.), and also acetates such as CH$_3$COONa or CH$_3$COOK.

Further suitable bases are alkali metal alcoholates such as sodium methylate, sodium propylate, potassium tert-butylate or sodium ethylate.

The addition of catalytic amounts of a crown ether, e.g. 18-crown-6 or 15-crown-5 has a favourable influence on the course of the reaction in the preparatory processes. Moreover, the catalytic use of tetraalkylamine salts, e.g. tetraalkylamino chlorides or bromides, preferably tetra-n-butylamino bromide, is advantageous for the same purpose. In addition, alkali metal iodides, preferably potassium iodide, may be used with advantage as catalysts.

In the preparatory processes, the reaction temperatures are in the range from 10° to 90° C., preferably from 30° to 80° C. The pressure ratios during the reaction are in the range from 1 to 20 mbar, preferably from 6 to 14 mbar.

The invention also relates to compositions for controlling plant-destructive nematodes and also for protecting plants from attack by nematodes, which compositions contain compounds of formula Ia, Ib or I*.

The present invention also relates to the preparation of nematicidal compositions, which comprises homogeneously mixing active ingredients of the formula Ia, Ib or I* with one or more of the carriers and adjuvants described herein. The invention further relates to a method of treating plants, which is characterised by the application of the compounds of formula Ia, Ib or I* or of the novel compositions.

Some of the starting compounds of formulae IIa and IIb are known, and some are novel. The novel compounds of formulae IIa and IIb are intermediates for the preparation of valuable nematicidal compounds (v. Table 0) and therefore constitute an object of the present invention.

The starting compounds of formulae IIa and IIb can be prepared by known methods as follows:

(a) The 2-mercapto-1,3,4-oxadiazoles can be obtained by adding carbon disulfide to a solution of the correspondingly substituted benzhydrazide in aqueous alcoholic potassium hydroxide and heating the reaction mixture for several hours. Suitable solvents are alcohols such as ethyl alcohol or n-amyl alcohol. Acidification of the resultant potassium salts yields the free mercapto compounds [q.v. J. Am. Chem. Soc. 78, pp. 4975–4978 (1956)].

(b) The 2-mercapto-1,3,4-thiadiazoles can be obtained by treating the correspondingly substituted benzoyl potassium dithiocarbazate with concentrated sulfuric acid at $-5°$ to 10° C. [q.v. J. prakt. Chem. 93, p. 49 (1916); J. Org. Chem. 23, p. 1021 (1958); J. Heterocycl. Chem. 19, pp. 542–544 (1982)].

A preferred method of using a compound of formula Ia, Ib or I* or a nematicidal composition containing at least one of these compounds is soil application comprising treating the locus of the plants with a liquid or solid formulation.

The compounds of formula Ia, Ib or I* may also be applied to seeds (dressing/coating) either by impregnating the seeds in a liquid formulation of the active ingredient or by coating them with a solid formulation. Moreover, in special cases further types of application are also possible, e.g. selective treatment of the plant stems or buds.

The compounds of formula Ia, Ib or I* are normally applied in the form of compositions and can be applied to the crop area or plant to be treated, simultaneously or in succession, with further compounds. These compounds can also include other compositions applied in agriculture which are used to increase production by promoting the growth of useful plants. Examples of such compositions are fertilisers, herbicides, insecticides, fungicides, mollusicides etc., or mixtures of several of these preparations, if desired, together with further carriers, surfactants or other application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

The compounds of formula Ia, Ib or I* are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, dusting, scattering or pouring, are chosen in accordance with the intended objectives and the prevailing circumstances. Advantageous rates of application are normally from 500 g to 6 kg of active ingredient (a.i.) per hectare, preferably from 1 to 4 kg a.i./ha.

The formulations, i.e. the compositions, preparations or mixtures containing the compound (active ingredient) of formula Ia, Ib or I* and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers are esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil, sunflower oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula Ia, Ib or I* to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylsulfonates.

The fatty sulfonates or sulfates are usually in the form of alkali metal salts, alkaline earth metal salts or unsubstituted or substituted ammonium salts and contain a $C_8-C_{22}$alkyl radical which also includes the alkyl moiety of acyl radicals, e.g. the sodium or calcium salt of lignosulfonic acid, or dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8-C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide.

The agrochemical compositions usually contain 0.1 to 99% by weight, preferably 0.1 to 95% by weight, of a compound of formula Ia, Ib or I*, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Such agrochemical compositions constitute an object of the present invention.

The invention is illustrated in more detail by the following non-limitative Examples.

1. PREPARATORY EXAMPLES

Example 1.1

Preparation of

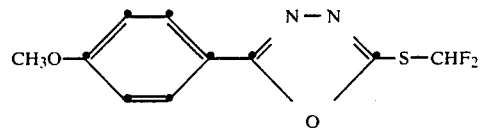

2-Difluoromethylthio-5-(4'-methoxyphenyl)-1,3,4,-oxadiazole (a) With stirring, 10.2 g of 2-mercapto-5-(4'-methoxyphenyl)-1,3,4-oxadiazole and 100 ml of dioxane are added to a solution of 4.5 g of potassium hydroxide in 18 ml of water. After the addition of 0.2 g of potassium iodide and 2 crystals of 18-crown-6, the mixture is heated to 50°-60° C. With good stirring, a weak stream of chlorodifluoromethane is then passed through the mixture for 6 hours. The reaction mixture is then subsequently concentrated by evaporation in vacuo. The residue remaining after evaporation is taken up in methylene chloride, and the resultant solution is washed in succession with water and 1n sodium hydroxide solution. The solvent is evaporated off, affording the title compound (recrystallised from cyclohexane) in the form of colourless crystals with a melting point of 95°-97° C.

(b) In an autoclave, 29.5 g of the potassium salt of 2-mercapto-5-(4'-methoxyphenyl)-1,3,4-oxadiazole are added to a mixture of 3.2 g of potassium hydroxide and 0.5 g of potassium iodide in 40 ml of water and 200 ml of dioxane. After thorough stirring, 51.9 g of chlorodifluoromethane are pressed in. The mixture is then heated, with stirring, for 18 hours at 45°-50° C. (10–12 bar). After cooling and release of pressure, the reaction mixture is poured into 500 ml of ice-water. The crystals are isolated by suction filtration and dried. Slightly yellowish crystals with a melting point of 93°-96° C. are obtained.

Example 1.2

Preparation of

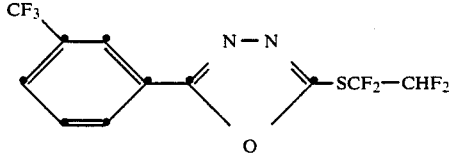

2-(1,1,2,2-Tetrafluoroethylthio)-5-(3'-trifluoromethylphenyl)-1,3,4-oxadiazole 60 ml of dimethylformamide and 7.38 g of 2-mercapto-5-(3'-trifluoromethylphenyl)-1,3,4-oxadiazole (m.p. 154°-155° C.) and 0.7 g of potassium hydroxide are stirred in an autoclave. 22 g of tetrafluoroethylene are pressed in, and the reaction mixture is heated for 19 hours at 60° C. (10–12·10$^5$ Pa). After cooling and release of pressure, the solution is poured into ice-water, the product is taken up in chloroform, the chloroform solution is washed with 1n sodium hydroxide solution, and the solvent is removed in vacuo, affording as reside the title compound in the form of an oil with a refractive index $n_D^{22}$ of 1.4926.

EXAMPLE 1.3

Preparation of

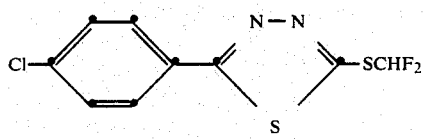

2-Difluoromethylthio-5-(4'-chlorophenyl)-1,3,4-thiadiazole 6.9 g of 2-mercapto-5-(4'-chlorophenyl)-1,3,4-thiadiazole and 60 ml fo dioxane are added to a solution of 2.4 g of potassium hydroxide in 10 ml of water. After the addition of 0.2 g of potassium iodide and 2 crystals of tetrabutylammonium bromide, the mixture is heated to 40° C. With stirring, a weak stream of chlorodifluoromethane is then passed through the mixture for 4 hours. The reaction mixture is then subsequently concentrated by evaporation in vacuo. The residue remaining after evaporation is taken up in methylene chloride, and the resultant solution is washed in succession with water and 1n sodium hydroxide solution. The solvent is evaporated off, affording the title compound (recrystallised from isopropanol) in the form of colourless crystals with a melting point of 74°-76° C.

Example 1.4

Preparation of

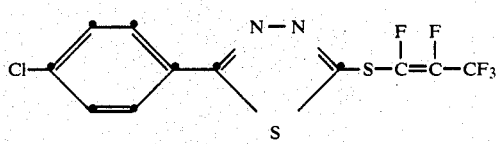

2-[1,2,3,3,3-Pentafluoropropen-1-ylthio]-5-(4-chlorophenyl)-1,3,4-thiadiazole 60 ml of dimethylformamide and 6.85 g of 5-(4-chlorophenyl)-2-mercapto-1,3,4-thiadiazole and 0.7 g of potassium hydroxide are stirred in an autoclave. 20 g of hexafluoropropylene are pressed in, and the reaction mixture is heated for 19 hours at 60° C. (10–12·10⁵ Pa). After cooling and release of pressure, the solution is poured into ice-water, the product is taken up in chloroform, the chloroform solution is washed with 1n sodium hydroxide solution, and the solvent is removed in vacuo, affording as reside the title compound in the form of an crystals with a melting point of 69°-70° C.

The following compounds of the present invention can be prepared by following the procedures of the Preparatory Examples and of the processes described above. The compounds listed below serve to illustrate the present invention and constitute no limitation thereof.

TABLE 0

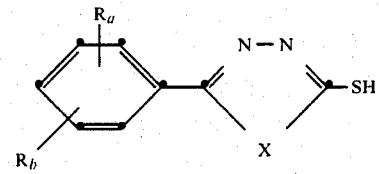

| Comp. | $R_a$ | $R_b$ | X | Physical data [m.p. 0° C.] |
|---|---|---|---|---|
| 0.1 | 3-CF₃ | H | O | 154–155 |
| 0.2 | 2-F | H | O | 174–176 |
| 0.3 | 2-CH₃ | 3-CH₃ | O | 170–172 |
| 0.4 | 2-CH₃ | 4-Cl | O | 196–198 |
| 0.5 | 3-CH₃ | H | O | 158–160 |
| 0.6 | 3-CH₃ | 5-CH₃ | O | 235–238 |
| 0.7 | 3-OCH₃ | H | O | 165–167 |
| 0.8 | 3-CH₃ | 4-CH₃ | O | 191–193 |
| 0.9 | 2-CH₃ | 5-CH₃ | O | 227–229 |
| 0.10 | 2-OCH₃ | H | O | 235–238 |
| 0.11 | 3-CF₃ | H | S | 173–176 |
| 0.12 | 2-Cl | 4-Cl | S | 228–230 |
| 0.13 | 2-F | H | S | 197–199 |
| 0.14 | 2-CH₃ | H | S | 164–166 |
| 0.15 | 4-CH₃ | H | S | 198 |
| 0.16 | 3-CH₃ | 5-CH₃ | S | 237–240 |
| 0.17 | 3-OCH₃ | H | S | 207–209 |
| 0.18 | 2-CH₃ | 5-CH₃ | S | 195 |
| 0.19 | 2-OCH₃ | H | S | 220–223 |
| 0.20 | 3-OCH₃ | 4-OCH₃ | S | 244–246 |
| 0.21 | 4-C₂H₅O | H | S | 203–206 |
| 0.22 | 2-F | 6-F | S | 190 |
| 0.23 | 4-t-C₄H₉ | H | S | 187–189° |
| 0.24 | 2-J | H | S | 176–178° |
| 0.25 | 2-Cl | 5-Cl | S | 223–225° |
| 0.26 | 3-Cl | 4-Cl | S | 226–228° |
| 0.27 | 4-CF₃ | H | S | 167–170° |
| 0.28 | 4-F | H | S | 210–212° |
| 0.29 | 3-Cl | 5-Cl | S | 239–241° |
| 0.30 | 2-CH₃ | 4-Cl | S | 212–215° |
| 0.31 | 3-CH₃ | 4-Cl | S | 213–216° |

TABLE 1

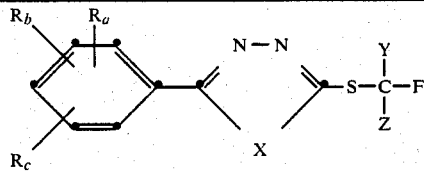

| Comp. | $R_a$ | $R_b$ | $R_c$ | X | Z | Y | Physical data |
|---|---|---|---|---|---|---|---|
| 1.1 | H | 4-OCH₃ | H | O | F | H | m.p. 95–97° C. |
| 1.2 | 3-CF₃ | H | H | O | F | CHF₂ | $n_D^{22}$ 1.4926 |
| 1.3 | H | 4-Cl | H | S | F | H | m.p. 74–76° C. |
| 1.4 | H | 4-CH₃ | H | O | F | H | m.p. 104–106° C. |
| 1.5 | 2-CH₃ | H | 6-CH₃ | O | F | H | $n_D^{22}$ 1.5550 |
| 1.6 | 3-CH₃ | 4-CH₃ | H | O | F | H | $n_D^{20}$ 1.5617 |
| 1.7 | 3-OCH₃ | H | H | O | F | H | $n_D^{22}$ 1.5528 |
| 1.8 | 2-OCH₃ | H | H | O | F | H | resin |
| 1.9 | 3-OCH₃ | 4-OCH₃ | 5-OCH₃ | O | F | H | $n_D^{22}$ 1.5339 |
| 1.10 | 2-CH₃ | H | 5-CH₃ | O | F | H | $n_D^{22}$ 1.5146 |
| 1.11 | 2-CH₃ | 3-CH₃ | H | O | F | H | $n_D^{22}$ 1.5653 |
| 1.12 | 3-CH₃ | H | H | O | F | H | m.p. 47–50° C. |

TABLE 1-continued

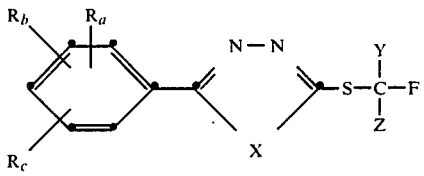

| Comp. | $R_a$ | $R_b$ | $R_c$ | X | Z | Y | Physical data |
|---|---|---|---|---|---|---|---|
| 1.13 | 3-$CH_3$ | H | 5-$CH_3$ | O | F | H | m.p. 44–46° C. |
| 1.14 | 3-$CF_3$ | H | H | O | F | H | $n_D^{22}$ 1.5188 |
| 1.15 | H | 4-Cl | H | O | F | H | m.p. 76–78° C. |
| 1.16 | 3-$CH_3$ | H | 5-$CH_3$ | O | F | $CHF_2$ | $n_D^{22}$ 1.5290 |
| 1.17 | 3-$CH_3$ | H | H | S | F | H | resin |
| 1.18 | H | 4-$OCH_3$ | H | S | F | H | m.p. 94–96° C. |
| 1.19 | 2-F | H | H | S | F | H | m.p. 45–47° C. |
| 1.20 | 3-$OCH_3$ | H | H | S | F | H | m.p. 38–41° C. |
| 1.21 | 2-$CH_3$ | H | 5-$CH_3$ | S | F | H | m.p. 77–79° C. |
| 1.22 | 3-$CF_3$ | H | H | S | F | H | $n_D^{22}$ 1.5568 |
| 1.23 | H | 4-$CH_3$ | H | S | F | H | m.p. 88–91° C. |
| 1.24 | 3-$CH_3$ | H | 5-$CH_3$ | S | F | H | $n_D^{22}$ 1.6037 |
| 1.25 | 2-$OCH_3$ | H | H | S | F | H | m.p. 63–65° C. |
| 1.26 | 2-$CH_3$ | H | H | S | F | H | $n_D^{22}$ 1.6094 |
| 1.27 | 2-Cl | 4-Cl | H | S | F | H | m.p. 79–81° C. |
| 1.28 | 2-F | H | 6-F | S | F | H | m.p. 41–42° C. |
| 1.29 | 3-$OCH_3$ | 4-$OCH_3$ | H | S | F | H | m.p. 129–131° C. |
| 1.30 | 3-$CH_3$ | 4-$CH_3$ | H | S | F | H | m.p. 42–44° C. |
| 1.31 | H | 4-$OC_2H_5$ | H | S | F | H | m.p. 94–96° C. |
| 1.32 | H | 4-t-$C_4H_9$ | H | S | F | H | m.p. 50–52° C. |
| 1.33 | 2-J | H | H | S | F | H | $n_D^{22}$ 1.6668 |
| 1.34 | 3-Cl | H | H | S | F | H | m.p. 41–43° C. |
| 1.35 | 2-Cl | H | 5-Cl | S | F | H | m.p. 85–87° C. |
| 1.36 | 3-Cl | 4-Cl | H | S | F | H | m.p. 56–59° C. |
| 1.37 | 2-Cl | H | H | S | F | H | $n_D^{23}$ 1.6217 |
| 1.38 | 2-$CH_3$ | 4-Cl | H | S | F | H | m.p. 51–52° C. |
| 1.39 | 2-Cl | H | 6-Cl | S | F | H | $n_D^{25}$ 1.5923 |
| 1.40 | H | 4-$CF_3$ | H | S | F | H | |
| 1.41 | H | 4-$OCH_3$ | H | S | F | F | |
| 1.42 | H | 4-$OCH_3$ | H | S | F | $CF_3$ | |
| 1.43 | H | 4-$OCH_3$ | H | S | $CF_3$ | $CF_3$ | |
| 1.44 | H | 4-$OCH_3$ | H | S | F | $HC(F)CF_3$ | |
| 1.45 | H | 4-$OCH_3$ | H | S | $CF_3$ | $CHF_2$ | |
| 1.46 | H | 4-$CH_3$ | H | S | F | F | |
| 1.47 | H | 4-$CH_3$ | H | S | F | $CF_3$ | |
| 1.48 | H | 4-$CH_3$ | H | S | $CF_3$ | $CF_3$ | |
| 1.49 | H | 4-$CH_3$ | H | S | F | $HC(F)CF_3$ | |
| 1.50 | H | 4-$CH_3$ | H | S | $CF_3$ | $CHF_2$ | |
| 1.51 | 3-$CH_3$ | H | H | S | F | F | |
| 1.52 | 3-$CH_3$ | H | H | S | F | $CF_3$ | |
| 1.53 | 3-$CH_3$ | H | H | S | $CF_3$ | $CF_3$ | |
| 1.54 | 3-$CH_3$ | H | H | S | F | $HC(F)CF_3$ | |
| 1.55 | 3-$CH_3$ | H | H | S | $CF_3$ | $CHF_2$ | |
| 1.56 | H | 4-Cl | H | S | F | F | |
| 1.57 | H | 4-Cl | H | S | F | $CF_3$ | |
| 1.58 | H | 4-Cl | H | S | $CF_3$ | $CF_3$ | |
| 1.59 | H | 4-Cl | H | S | F | $HC(F)CF_3$ | |
| 1.60 | H | 4-Cl | H | S | $CF_3$ | $CHF_2$ | |
| 1.61 | 2-F | H | 6-F | S | F | F | |
| 1.62 | 2-F | H | 6-F | S | F | $HC(F)CF_3$ | |
| 1.63 | 2-F | H | 6-F | S | $CF_3$ | $CF_3$ | |
| 1.64 | 2-F | H | 6-F | S | F | $CF_3$ | |
| 1.65 | 2-F | H | 6-F | S | $CF_3$ | $CHF_2$ | |
| 1.66 | 2-F | H | 6-F | O | F | H | |
| 1.67 | 2-F | H | 6-F | O | F | F | |
| 1.68 | H | 4-F | H | S | F | H | m.p. 59–60° C. |
| 1.69 | 3-Cl | H | 5-Cl | S | F | H | m.p. 68–70° C. |
| 1.70 | 3-$CH_3$ | 4-Cl | H | S | F | H | m.p. 42–44° C. |
| 1.71 | 3-Br | H | H | S | F | H | m.p. 43–45° C. |
| 1.72 | 3-F | H | H | S | F | H | m.p. 37–38° C. |

TABLE 2

$$\begin{array}{c} R_b \\ R_a \\ \diagdown \\ \diagup \\ R_c \end{array} \!\!\!\! \diagup\!\!\!\!\diagdown \!\!\!\! \begin{array}{c} N-N \\ \diagdown \\ X \end{array} \!\!\!\! \begin{array}{c} F\ F \\ | \ | \\ S-C=C-Z \end{array}$$

| Comp. | $R_a$ | $R_b$ | $R_c$ | X | Z | Physical data |
|---|---|---|---|---|---|---|
| 2.1 | H | 4-Cl | H | S | $CF_3$ | m.p. 69–70° C. |
| 2.2 | 2-F | H | 6-F | S | $CF_3$ | |
| 2.3 | H | 4-F | H | S | F | |
| 2.4 | 3-Cl | H | H | S | $CF_3$ | |
| 2.5 | H | 4-$CH_3O$ | H | O | $CF_3$ | |
| 2.6 | 3-F | H | H | S | F | |
| 2.7 | 2-$CH_3$ | H | H | O | $CF_3$ | |
| 2.8 | 2-F | H | 6-F | S | F | |

2. FORMULATION EXAMPLES FOR LIQUID ACTIVE INGREDIENTS OF FORMULA Ia, Ib OR I*

(throughout, percentages are by weight)

| 2.1. Emulsifiable concentrates | a | b | c |
|---|---|---|---|
| a compound of Table 1 or 2 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2. Solutions | a | b | c | d |
|---|---|---|---|---|
| a compound of Table 1 or 2 | 80% | 10% | 5% | 95% |
| ethylene glycol monomethyl ether | 20% | — | — | — |
| polyethylene glycol (mol. wt. 400) | — | 70% | — | — |
| N—methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of microdrops.

| 2.3. Granulates | a | b |
|---|---|---|
| a compound of Table 1 or 2 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | a | b |
|---|---|---|
| a compound of Table 1 or 2 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

FORMULATION EXAMPLES FOR SOLID ACTIVE INGREDIENTS OF FORMULA Ia, Ib OR I*

(throughout, percentages are by weight)

| 2.5. Wettable powders | a | b | c |
|---|---|---|---|
| a compound of Table 1 or 2 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| a compound of Table 1 or 2 | 10% |
| octylphenol polyethlene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Dusts | a | b |
|---|---|---|
| a compound of Table 1 or 2 | 5% | 8% |
| talcum | 95% | — |
| kaolin | — | 92% |

Ready-for-use dusts are obtained by mixing the active ingredient with the carrier, and grinding the mixture in a suitable mill.

| 2.8. Extruder granulate | |
|---|---|
| a compound of Table 1 or 2 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Table 1 or 2 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| a compound of Table 1 or 2 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

BIOLOGICAL EXAMPLE

3.1 Action against *Meloidogyne incognita*

Eggs of *Meloidogyne incognita* are mixed into sand. This mixture is then placed in 200 ml earthenware pots (5000 eggs per pot). On the same day a three-week-old tomato plant is planted in each pot and the formulated active ingredient is introduced into the pots by pressure application (0.002% active ingredient, based on the volume of the soil). The potted plants are stood in a greenhouse at a temperature of 26±1° C. and a relative humidity of 60%. After 4 weeks evaluation is made by examining the plants for rood-knot formation in accordance with the Knot Index.

Compounds of Tables 1 and 2 exhibit good activity against Meloidogyne incognita in that they substantially reduce root-knot formation. On the other hand, untreated and infected control plants display severe root-knot formation (=100%). Thus, in this test, e.g. compounds 1.1, 1.3. and 1.28 reduce root-knot formation almost completely (0–10% attack).

What is claimed is:

1. A compound of formula Ia

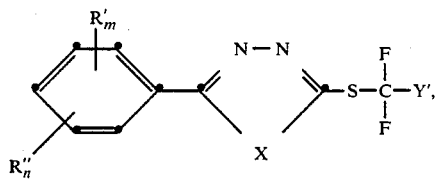

wherein
R' is $C_1$–$C_5$alkyl, $C_1$–$C_5$alkoxy, halogen or trifluoromethyl,
R" is $C_1$–$C_5$alkyl or halogen,
m is 1 to 3 and n is 0 or 1,
X is oxygen or sulfur and
Y' is hydrogen or the group $CHF_2$, or an acid addition salt thereof.

2. A compound of formula Ib

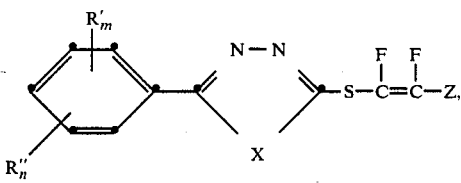

wherein
R' is $C_1$–$C_5$alkyl, $C_1$–$C_5$alkoxy, halogen or trifluoromethyl,
R" is $C_1$–$C_5$alkyl or halogen,
m is 1 to 3 and n is 0 or 1,
X is oxygen or sulfur and
Z is fluorine or trifluoromethyl, or an acid addition salt thereof.

3. A compound of formula I*

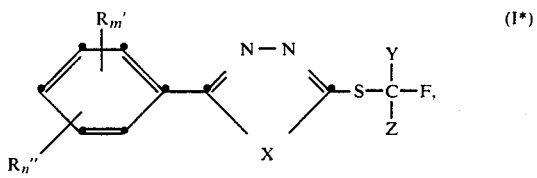

wherein
R' is $C_1$–$C_5$alkyl, $C_1$–$C_5$alkoxy, halogen or trifluoromethyl,
R" is $C_1$–$C_5$alkyl or halogen,
m is 1 to 3 and n is 0 or 1,
X is oxygen or sulfur,
Y is hydrogen, fluorine, trifluoromethyl or the group HC(F)Z and
Z is fluorine or trifluoromethyl, or an acid addition salt thereof.

4. A compound of formula Ia according to claim 1, wherein R' is $C_1$–$C_2$alkyl, $C_1$–$C_2$alkoxy, halogen or trifluoromethyl and R" is $C_1$–$C_4$alkyl or halogen, m is 1 or 2 and X, Y' and n are as defined for formula Ia.

5. A compound of formula Ia according to claim 1, wherein R' is methyl, methoxy, fluorine or chlorine and R" is fluorine or chlorine, Y' is hydrogen and X and n are as defined for formula Ia.

6. A compound of formula Ib according to claim 2, wherein R' is $C_1$–$C_2$alkyl, $C_1$–$C_2$alkoxy, halogen or trifluoromethyl and R" is $C_1$–$C_4$alkyl or halogen, m is 1 or 2 and X, Z and n are as defined for formula Ib.

7. A compound of formula Ib according to claim 2, wherein R' is methyl, methoxy, fluorine or chlorine and R" is fluorine or chlorine, Z is fluorine and X and n are as defined for formula Ib.

8. A compound of formula I* according to claim 3, wherein R' is $C_1$–$C_2$alkyl, $C_1$–$C_2$alkoxy, halogen or trifluoromethyl and R" is $C_1$–$C_4$alkyl or halogen, m is 1 or 2 and X, Y, Z and n are as defined for formula I*.

9. A compound of formula I* according to claim 3, wherein R' is methyl, methoxy, fluorine or chlorine and R" is fluorine or chlorine, Y is hydrogen and Z is fluorine and X and n are as defined for formula I*.

10. A compound selected from the group consisting of
2-difluoromethylthio-5-(4'-methoxyphenyl)-1,3,4-oxadiazole;
2-difluoromethylthio-5-(4'-methoxyphenyl)-1,3,4-thiadiazole;
2-difluoromethylthio-5-(2'-fluorophenyl)-1,3,4-thiadiazole;
2-difluoromethylthio-5-(4'-chlorophenyl)-1,3,4-thiadiazole;
2-difluoromethylthio-5-(2'-methylphenyl)-1,3,4-thiadiazole;
2-difluoromethylthio-5-(2',4'-dichlorophenyl)-1,3,4-thiadiazole;
2-difluoromethylthio-5-(2',6'-difluorophenyl)-1,3,4-thiadiazole;

2-difluoromethylthio-5-(4'-fluorophenyl)-1,3,4-thiadiazole;

2-difluoromethylthio-5-(3'-chlorophenyl)-1,3,4-thiadiazole.

11. A pesticidal composition for controlling nematodes or for protecting plants from attack by nematodes, which composition contains as active ingredient at least one compound of formula Ia as defined in claim 1.

12. A pesticidal composition for controlling nematodes or for protecting plants from attack by nematodes, which composition contains as active ingredient at least one compound of formula Ib as defined in claim 2.

13. A pesticidal composition for controlling nematodes or for protecting plants from attack by nematodes, which composition contains as active ingredient at least one compound of formula I* as defined in claim 3.

14. A method of controlling nematodes or of protecting cultivated plants from attack by namtodes, which method comprises applying to the plant or to the locus thereof a compound of formula Ia as defined in claim 1.

15. A method of controlling nematodes or of protecting cultivated plants from attack by nematodes, which method comprises applying to the plant or to the locus thereof a compound of formula Ib as defined in claim 2.

16. A method of controlling nematodes or of protecting cultivated plants from attack by nematodes, which method comprises applying to the plant or to the locus thereof a compound of formula I* as defined in claim 3.

* * * * *